US008054454B2

(12) United States Patent
Treado et al.

(10) Patent No.: US 8,054,454 B2
(45) Date of Patent: *Nov. 8, 2011

(54) TIME AND SPACE RESOLVED STANDOFF HYPERSPECTRAL IED EXPLOSIVES LIDAR DETECTOR

(75) Inventors: Patrick I Treado, Pittsburgh, PA (US); Matthew P. Nelson, Harrison City, PA (US); Jason Neiss, Pittsburgh, PA (US); Hugh W. Hubble, II, Swissvale, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/199,145

(22) Filed: Aug. 27, 2008

(65) Prior Publication Data

US 2009/0128802 A1    May 21, 2009

Related U.S. Application Data

(63) Continuation of application No. 11/450,149, filed on Jun. 9, 2006.

(60) Provisional application No. 60/699,251, filed on Jul. 14, 2005, provisional application No. 60/786,978, filed on Mar. 29, 2006.

(51) Int. Cl.
 *G01N 21/00* (2006.01)
(52) U.S. Cl. ........... 356/73; 356/301; 356/318; 356/445
(58) Field of Classification Search .............. 356/72–73, 356/317–318, 417, 445, 301
 See application file for complete search history.

(56) References Cited

U.S. PATENT DOCUMENTS

| 3,679,307 | A | * | 7/1972 | Zoot et al. ........................ 356/2 |
| 4,711,577 | A | * | 12/1987 | Hull-Allen ..................... 356/624 |
| 4,952,816 | A | * | 8/1990 | Dunning ................... 250/559.31 |
| 5,216,484 | A | * | 6/1993 | Chao et al. .................... 356/326 |
| 5,528,368 | A | * | 6/1996 | Lewis et al. ................. 250/458.1 |
| 5,606,164 | A |   | 2/1997 | Price et al. |
| 6,006,140 | A | * | 12/1999 | Carter ............................. 700/56 |
| 6,008,492 | A | * | 12/1999 | Slater et al. ................... 250/334 |

(Continued)

FOREIGN PATENT DOCUMENTS

EP         2083259      7/2009

(Continued)

OTHER PUBLICATIONS

Nelson et al, "Single-Shot Muitiwavelength Imaging of Laser Plums," Applied Spectroscopy, vol. 52, No. 2, 1998.

(Continued)

*Primary Examiner* — Kara E Geisel

(57) ABSTRACT

A system and method for standoff detection of explosives and explosive residue. A laser light source illuminates a target area having an unknown sample producing luminescence emitted photons, scattered photons and plasma emitted photons. A first optical system directs light to the target area. A video capture device outputs a dynamic image of the target area. A second optical system collects photons, and directs collected photons to a first two-dimensional array of detection elements and/or to a fiber array spectral translator device which device includes a two-dimensional array of optical fibers drawn into a one-dimensional fiber stack. A spectrograph is coupled to the one-dimensional fiber stack of the fiber array spectral translator device, wherein the entrance slit of the spectrograph is coupled to the one dimensional fiber stack.

10 Claims, 13 Drawing Sheets

U.S. PATENT DOCUMENTS

| | | | |
|---|---|---|---|
| 6,075,891 | A | 6/2000 | Burman |
| 6,208,749 | B1* | 3/2001 | Gutkowicz-Krusin et al. ............................ 356/303 |
| 6,274,871 | B1* | 8/2001 | Dukor et al. ............ 250/339.08 |
| 6,421,553 | B1 | 7/2002 | Costa et al. |
| 6,717,668 | B2 | 4/2004 | Treado |
| 6,967,612 | B1 | 11/2005 | Gorman |
| 6,985,216 | B2 | 1/2006 | Treado et al. |
| 6,992,809 | B1 | 1/2006 | Wang |
| 7,012,695 | B2 | 3/2006 | Maier et al. |
| 7,019,296 | B2 | 3/2006 | Treado et al. |
| 7,061,606 | B2 | 6/2006 | Treado et al. |
| 7,068,357 | B2 | 6/2006 | Treado et al. |
| 7,072,770 | B1 | 7/2006 | Schweitzer et al. |
| 7,088,435 | B2* | 8/2006 | Brestel et al. ..................... 356/72 |
| 7,123,360 | B2 | 10/2006 | Treado et al. |
| 7,268,861 | B2 | 9/2007 | Treado et al. |
| 7,268,862 | B2 | 9/2007 | Treado et al. |
| 7,277,178 | B2 | 10/2007 | Shpantzer |
| 7,295,308 | B1* | 11/2007 | Samuels ....................... 356/326 |
| RE39,977 | E | 1/2008 | Treado et al. |
| 7,317,516 | B2 | 1/2008 | Treado et al. |
| 7,322,267 | B1 | 1/2008 | Munson |
| 7,362,489 | B2 | 4/2008 | Wang |
| 7,362,839 | B2 | 4/2008 | Goth |
| 7,409,299 | B2 | 8/2008 | Schweitzer et al. |
| 7,417,727 | B2 | 8/2008 | Polonskiy |
| 7,417,796 | B2 | 8/2008 | Wang |
| 7,420,664 | B2 | 9/2008 | Treado |
| 7,420,675 | B2 | 9/2008 | Giakos |
| 7,436,500 | B2 | 10/2008 | Treado et al. |
| 7,479,966 | B2 | 1/2009 | Maier et al. |
| 7,502,188 | B2 | 3/2009 | Inomata |
| 7,511,624 | B2 | 3/2009 | Shaw |
| 7,525,102 | B1 | 4/2009 | Henshaw |
| 7,551,715 | B2 | 6/2009 | Rothschild |
| 7,679,740 | B2 | 3/2010 | Neiss et al. |
| 7,705,981 | B2 | 4/2010 | Maier et al. |
| 2001/0052979 | A1* | 12/2001 | Treado et al. ................. 356/326 |
| 2003/0085348 | A1 | 5/2003 | Megerle |
| 2003/0123056 | A1 | 7/2003 | Barnes |
| 2004/0051867 | A1 | 3/2004 | Brestel et al. |
| 2005/0105099 | A1 | 5/2005 | Shpantzer |
| 2005/0137806 | A1 | 6/2005 | Kutsyy et al. |
| 2005/0264813 | A1 | 12/2005 | Giakos |
| 2006/0077377 | A1 | 4/2006 | Brestel et al. |
| 2006/0100524 | A1 | 5/2006 | Lucassen et al. |
| 2006/0170922 | A1 | 8/2006 | Wang et al. |
| 2006/0203238 | A1 | 9/2006 | Gardner et al. |
| 2006/0219937 | A1 | 10/2006 | Henry et al. |
| 2006/0254522 | A1 | 11/2006 | Shaw |
| 2006/0256330 | A1* | 11/2006 | Leipertz ....................... 356/301 |
| 2006/0262304 | A1 | 11/2006 | Carron |
| 2007/0007384 | A1 | 1/2007 | Sliwa |
| 2007/0098142 | A1 | 5/2007 | Rothschild |
| 2007/0125951 | A1 | 6/2007 | Snider |
| 2007/0127030 | A1 | 6/2007 | Shpantzer |
| 2007/0139772 | A1 | 6/2007 | Wang |
| 2007/0153268 | A1 | 7/2007 | Panza et al. |
| 2007/0166045 | A1 | 7/2007 | Wang |
| 2007/0192035 | A1 | 8/2007 | Schweitzer et al. |
| 2007/0268485 | A1 | 11/2007 | Polonskiy |
| 2008/0036593 | A1 | 2/2008 | Rose-Pehrsson |
| 2008/0062353 | A1 | 3/2008 | Wang |
| 2008/0084553 | A1 | 4/2008 | Neiss et al. |
| 2008/0129581 | A1 | 6/2008 | Douglass |
| 2008/0144885 | A1 | 6/2008 | Zucherman |
| 2008/0165344 | A1 | 7/2008 | Treado et al. |
| 2008/0191137 | A1 | 8/2008 | Poteet |
| 2008/0192246 | A1 | 8/2008 | Neiss et al. |
| 2008/0198365 | A1 | 8/2008 | Treado |
| 2008/0204757 | A1 | 8/2008 | Manning |
| 2008/0258071 | A1 | 10/2008 | Arnold |
| 2008/0268548 | A1 | 10/2008 | Zuckerman |
| 2008/0295783 | A1 | 12/2008 | Furton |
| 2008/0300826 | A1 | 12/2008 | Schweitzer et al. |
| 2009/0012723 | A1 | 1/2009 | Treado et al. |
| 2009/0021730 | A1 | 1/2009 | Maier et al. |
| 2009/0043514 | A1 | 2/2009 | Schweitzer et al. |
| 2009/0046393 | A1 | 2/2009 | Davey |
| 2009/0066947 | A1 | 3/2009 | Bangalore et al. |
| 2009/0095885 | A1 | 4/2009 | Hager |
| 2009/0101843 | A1 | 4/2009 | Henshaw |
| 2009/0128802 | A1 | 5/2009 | Treado et al. |
| 2009/0202128 | A1* | 8/2009 | Gorian et al. ................. 382/132 |
| 2009/0236528 | A1 | 9/2009 | Shpantzer |
| 2009/0252650 | A1 | 10/2009 | Lakshmanan |
| 2009/0257555 | A1 | 10/2009 | Chalmers |
| 2010/0051809 | A1 | 3/2010 | Onat et al. |

FOREIGN PATENT DOCUMENTS

| | | |
|---|---|---|
| WO | PCT/US05/25112 | 2/2006 |
| WO | PCT/IB2006/052448 | 1/2007 |
| WO | PCT/US2005/036593 | 1/2007 |
| WO | PCT/US2006/027172 | 3/2007 |
| WO | PCT/US2006/060158 | 3/2007 |
| WO | PCT/US2005/033740 | 4/2007 |
| WO | PCT/US2006/012300 | 4/2007 |
| WO | PCT/US2006/060683 | 5/2007 |
| WO | PCT/US2005/044648 | 7/2007 |
| WO | PCT/US2006/022647 | 11/2007 |
| WO | PCT/US2007/015132 | 3/2008 |
| WO | PCT/US2007/018347 | 4/2008 |
| WO | PCT/US2007/081551 | 4/2008 |
| WO | PCT/US2007/016040 | 8/2008 |

OTHER PUBLICATIONS

Extended European Search Report, PCT/US2006/022647, mailed on Aug. 10, 2010.

Onat, Bora M. et al., A Solid State Hyperspectral Imager for Real-Time Standoff Explosives Detection Using Shortwave Infrared Imaging, Proc. of SPIE vol. 7310, 731004-1 to 731004.11, 2009.

Sharma, S.K. et al., Combined Remote LIBS and Raman Spectroscopy of Minerals Using a Single Laser Source, Lunar Planet Sci. XXXVIII, 2007.

Clegg, S.M. et al., LIBS-Raman Spectroscopy of Minerals Using Remote Surface Modification Techniques, Mar. 2006, Lunar Planet Sci. XXXVII.

Thompson, J. et al., Combined Remote LIBS and Raman Spectroscopy Measurements, Lunar Planet Sci, XXXVI, 2005.

Weins, R.C., Development of a Prototype Laser-Induced Breakdown Spectroscopy (LIBS) Instrument and Stand-off Raman Capabilities as Part of the Mars Instrument Development Program, Lunar Planet Sci., XXXI, 2000.

Poster-Session: Mars Polar Science, Astrobiology, Future Missions/Instruments and Other Mars Science, Jul. 2007. Secenth International Conference on Mars, Session 11.

Marquardt, Brian J. et al., Novel Probe for Laser-Induced Breakdown Spectroscopy and Raman Measurements Using an Imaging Optical Fiber (Jun. 1998) vol. 52, No. 9.

U.S. Appl. No. 12/430,581, Apr. 27, 2009.
U.S. Appl. No. 11/544,727, Oct. 10, 2006.
U.S. Appl. No. 12/504,914, Jul. 17, 2009.
U.S. Appl. No. 12/441,420, Jul. 14, 2010.
Office Action, U.S. Appl. No. 11/632,471, Feb. 17, 2008.
Office Action, U.S. Appl. No. 11/632,471, Apr. 12, 2009.
Office Action, U.S. Appl. No. 11/632,471, Apr. 16, 2008.
Office Action, U.S. Appl. No. 11/645,132, Apr. 1, 2009.

Sharma et al., "Stand-Off Raman Spectroscopic Detection of Minerals on Planetary Surfaces," Hawaii Institute of Geophysics and Planetology, pp. 2391-2407, 2003.

Sharma et al., "Portable Stand-Off Raman and Mie-Rayleigh LIDAR for Cloud, Aerosols, and Chemical Monitoring," Proceedings of SPIE vol. 5154, LIDAR Remote Sensing for Environmental Monitoring IV, pp. 1-14, 2003.

Sharma et al, "Remote Pulsed Laser Raman Spectroscopy Systems for Mineral Analysis on Planetary Surfaces to 66 Meters," Applied Spectroscopy, vol. 56, No. 6, 2002, pp. 699-705.

PCT/US06/22647, Notification of Transmittal of the International Search Report and the Written Opinion of the International Searching Authority, Mar. 31, 2008.

* cited by examiner

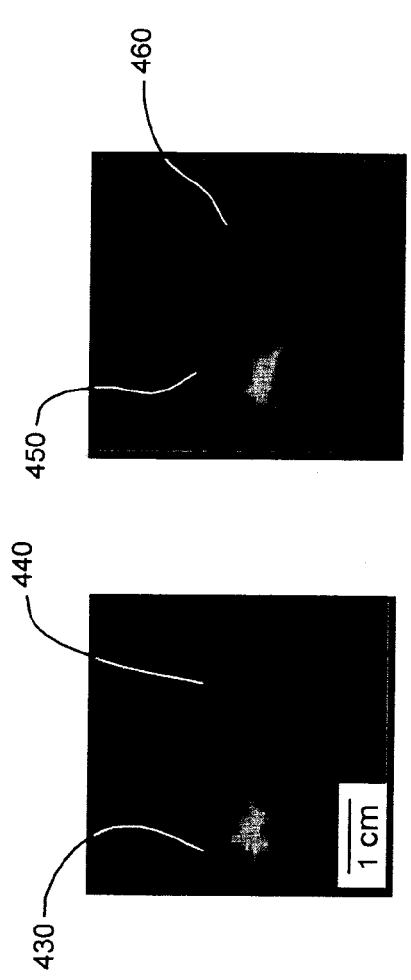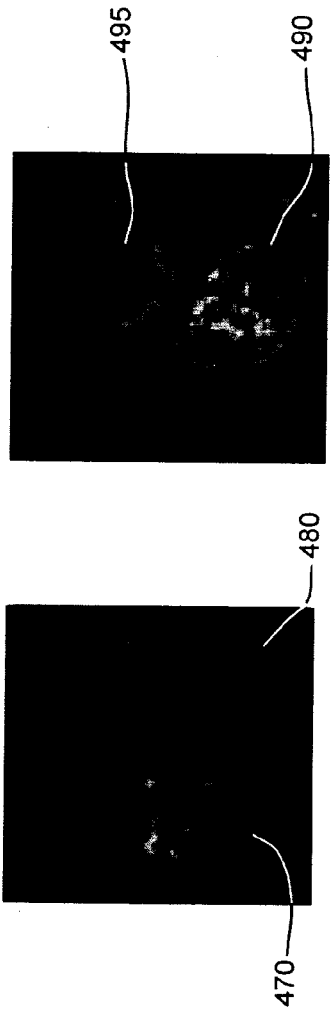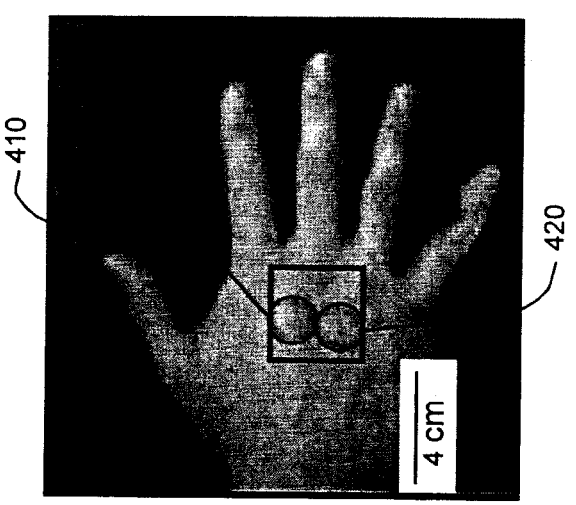
FIG. 4C
FIG. 4E
FIG. 4B
FIG. 4D
FIG. 4A

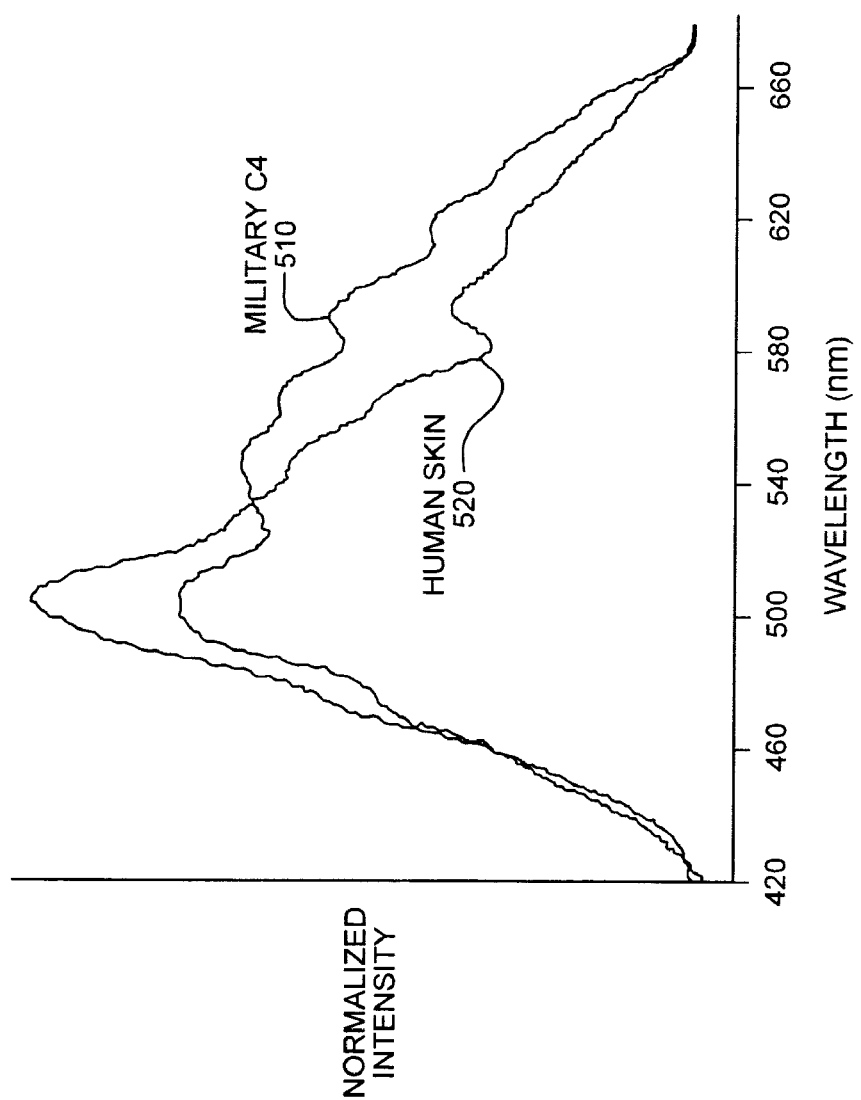

TIME AND SPACE RESOLVED STANDOFF HYPERSPECTRAL IED EXPLOSIVES LIDAR DETECTOR

RELATED APPLICATIONS

This application is a continuation of U.S. patent application Ser. No. 11/450,149 filed on Jun. 9, 2006 entitled Time and Space Resolved Standoff Hyperspectral IED Explosives LIDAR Detection which, in turn, claims the benefit of U.S. Patent Application No. 60/699,251 filed Jul. 14, 2005 entitled SHIELD: Standoff Hyperspectral Imaging Explosives LIDAR Detector/Optical Standoff Detection of Explosive Residue, and U.S. Patent Application No. 60/786,978 filed Mar. 29, 2006 entitled Time and Space Resolved Standoff Hyperspectral IED Explosives LIDAR Detection (TSR-SHIELD). The disclosures of all of these applications are incorporated herein by reference in their entireties.

FIELD OF DISCLOSURE

This application relates generally to systems and methods for detection of explosive material and residue of explosive material.

SUMMARY

The present disclosure provides for a system and method for standoff detection of explosives and explosive residue. A laser light source is configured to illuminate a target area having an unknown sample producing luminescence emitted photons, scattered photons and plasma emitted photons from different locations on or within the unknown sample. A first optical system is optically coupled to the laser light source to direct light to the target area having the unknown sample. A video capture device outputs a dynamic image of the target area. A second optical system collects the luminescence emitted, the scattered, and the plasma emitted photons, and directs the collected luminescence emitted photons to a first two-dimensional array of detection element. The second optical system further directs the collected scattered and plasma emitted photons to a fiber array spectral translator device. The first two-dimensional array of detection elements detects in a spatially accurate manner the luminescence emitted photons received from the second optical system and generates at least one of the following: a plurality of spatially resolved fluorescence spectra, and a plurality of spatially accurate wavelength resolved fluorescence images. The fiber array spectral translator device outputs at least one of the following received from the second optical system: the collected plasma emitted photons, and the collected scattered photons. The device includes a two-dimensional array of optical fibers drawn into a one-dimensional fiber stack so as to effectively convert a two-dimensional field of view into a curvilinear field of view. A photodiode is optically coupled to the first optical system and generates a gating signal to synchronize an acquisition time of a second two dimensional array of detection elements with a pulse width of the laser light emanating from the laser light source. A spectrograph is coupled to the one-dimensional fiber stack of the fiber array spectral translator device, wherein the entrance slit of the spectrograph is optically coupled to the one dimensional fiber stack. The spectrograph disperses the plasma emitted photons output by the fiber array spectral translator device to generate a plurality of spatially resolved Raman spectra. It also disperses the scattered photons output by the fiber array spectral translator device to generate a plurality of spatially resolved atomic spectra. The second two dimensional array of detection elements is optically coupled to the spectrograph and detects the plurality of spatially resolved Raman spectra and the plurality of spatially resolved atomic spectra produced by the spectrograph.

The present disclosure further provides for a method for detecting explosive material above ground. An above ground area is surveyed to identify a region of interest based on at least one of size, shape and color of the region of interest. The region of interest is illuminated with a plurality of photons to thereby produce emitted photons from the region of interest. The emitted photons, produced by the region of interest, are analyzed using fluorescence spectroscopy to produce at least one of the following: a plurality of spatially resolved fluorescence spectra and a plurality wavelength resolved fluorescence images. To identify a target area, the plurality of spatially resolved fluorescence spectra and the plurality wavelength resolved fluorescence images are used. The target area is illuminated with a plurality of photons to thereby produce Raman scattered photons and plasma emitted photons from the target area. Using a fiber array spectral translator device, Raman scattered photons and plasma emitted photons are collected. The device comprises a two dimensional non-linear array of optical fibers drawn into a one dimensional fiber stack that converts a two-dimensional field of view into a curvilinear field of view, wherein the one dimensional fiber stack is coupled to an entrance slit of an imaging spectrometer. The Raman scattered photons, produced by the target area, are analyzed using Raman spectroscopy to produce a plurality of spatially resolved Raman spectra. The plasma emitted photons, produced by the target area, are analyzed using laser induced breakdown spectroscopy to produce a plurality of spatially resolved atomic spectra. A fusion algorithm is applied to at least two of the following to identify one or more chemical compounds in the target area: the plurality of spatially resolved fluorescence spectra, the plurality of spatially resolved Raman spectra and the plurality of spatially resolved atomic spectra.

The present disclosure further provides for a method for detecting explosive material underground. An above ground area is surveyed to identify a region of interest based on at least one of size, shape and color of the region of interest. The region of interest is illuminated with a plurality of photons to thereby produce reflected photons from the region of interest. The reflected photons, produced by the region of interest, are analyzed using near infrared spectroscopy to produce at least one of the following: a plurality of spatially resolved near infrared spectra and a plurality wavelength resolved near infrared images. To identify a target area, the plurality of spatially resolved near infrared spectra and the plurality wavelength resolved near infrared images are used. The target area is illuminated with a plurality of photons to thereby produce Raman scattered photons and plasma emitted photons from the target area. Using a fiber array spectral translator device, Raman scattered photons and plasma reflected photons are collected. The device comprises a two dimensional non-linear array of optical fibers drawn into a one dimensional fiber stack that converts a two-dimensional field of view into a curvilinear field of view, wherein the one dimensional fiber stack is coupled to an entrance slit of an imaging spectrometer. The Raman scattered photons, produced by the target area, are analyzed using Raman spectroscopy to produce a plurality of spatially resolved Raman spectra. The plasma emitted photons, produced by the target area, are analyzed using laser induced breakdown spectroscopy to produce a plurality of spatially resolved atomic spectra. A fusion algorithm is applied to at least two of the following to identify one or more chemical compounds in the target area:

the plurality of spatially resolved near infrared spectra, the plurality of spatially resolved Raman spectra and the plurality of spatially resolved atomic spectra.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings:

FIGS. 4A-4E illustrate fluorescence images C4 on human skin;

FIGS. 5A and 5B illustrate fluorescence and Raman spectra of C4 and human skin flakes;

DESCRIPTION OF THE EMBODIMENTS

Reference will now be made in detail to the embodiments of the present disclosure, examples of which are illustrated in the accompanying drawings. Wherever possible, the same reference numbers will be used throughout the drawings to refer to the same or like parts.

Figure 1:
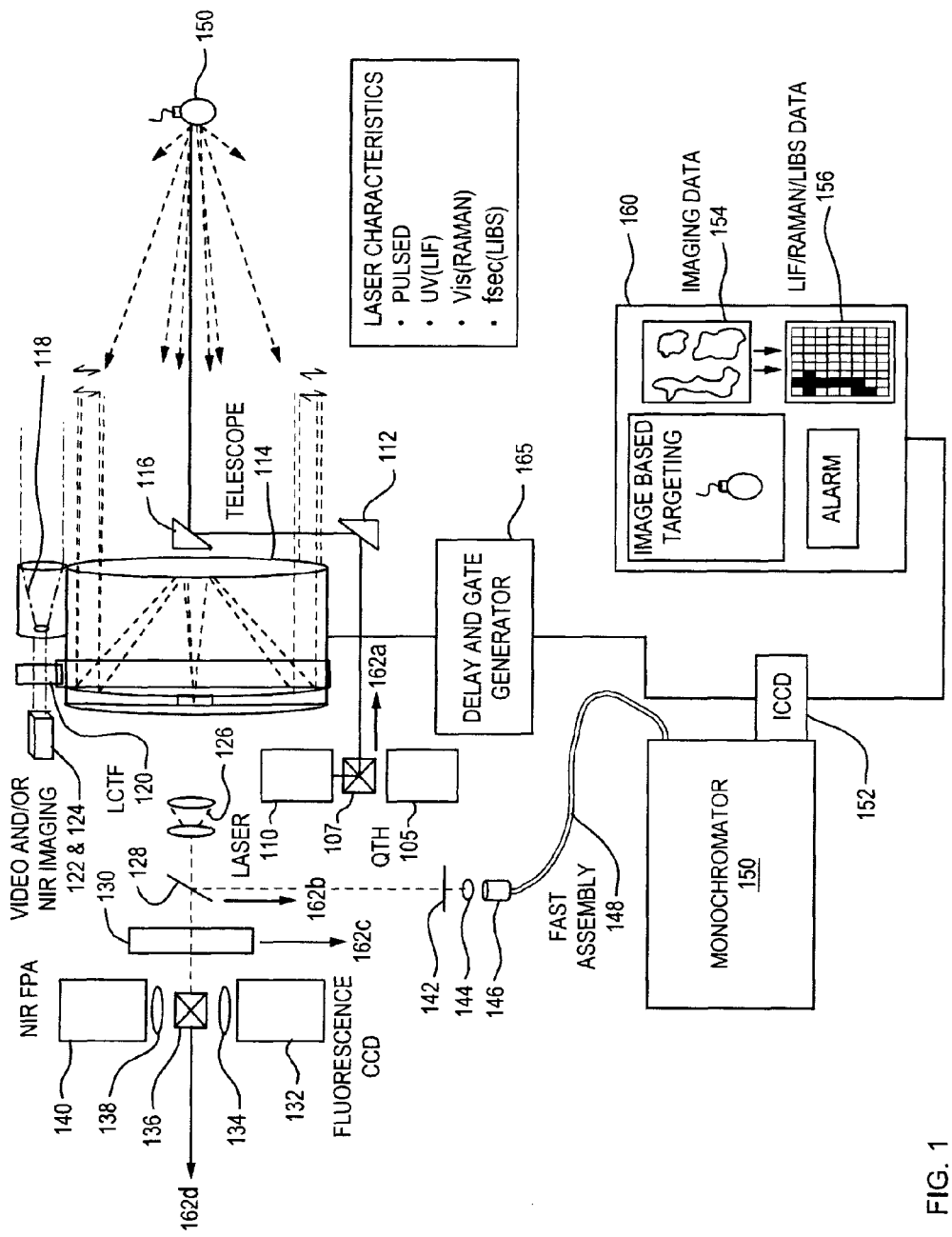
FIG. 1 illustrates a system of the present disclosure.

FIG. 1 illustrates an exemplary system 100 which may be used to carry out the methods of the present disclosure. System 100 may operate in a plurality of modes including a first order video targeting mode, a second order targeting mode and an imaging identification mode. The video targeting mode uses a video capture device 124 for rapidly screening regions of interest. The second order targeting mode operates in a fluorescence mode, an infrared mode or a combined fluorescence and infrared mode to survey target areas for the presence of unknown materials. The imaging identification mode operates in a Raman mode and a laser induced breakdown spectroscopy ("LIBS") mode to provide greater specificity in the identification of the unknown material. The unknown material is found in a target area 150 which may be found in a region of interest including above the ground surface or below ground surface. In one embodiment, the unknown material comprises an explosive material.

With reference to FIG. 1, system 100 includes light source to illuminate the target area having an unknown sample. The light source includes a laser light source 106 which illuminates the unknown sample with a plurality of photons to produce luminescence emitted photons, scattered photons, and plasma emitted photons from different locations on or within the unknown sample. In one embodiment, the laser light source 106 includes a femtosecond Nd:YAG pulsed light source illuminating the sample at a first wavelength of 1064 nm to produce plasma emitted photons, illuminates the sample at a second wavelength of 532 nm to produce Raman scattered and illuminates the sample at a third wavelength of 266 nm to produce luminescence emitted photons. In yet another embodiment, the laser light source 106 provides structured illumination wherein the spot size and geometry of the laser beam is controlled by control signals generated by processor 160. In an embodiment the specifications of the laser beam include: pulse length of 7 nanoseconds (ns), beam size of 2.8 millimeters (mm), beam divergence of <6 milliradians (mrad). For a laser beam propagating in free-space, the laser beam size is dependant on distance from the laser head and can be estimated: 2.8 mm+([range](mm)×tan(0.006)).

The femtosecond Nd:YAG laser results in femtosecond Raman scattered photons. These photons may provide enhanced S/N through the minimization of non-specific broadband fluorescence and luminescence. Most femtosecond Raman techniques thus far have been based on a pump-probe approach. Femtosecond Raman scattered photons will be measured using a conventional single pulse arrangement with appropriate filters to block broadband femtosecond response.

In addition to enhanced Raman, high intensity femtosecond lasers bring unique benefits to LIBS detection of explosives. The ultrashort LIBS plasma liberates only nanometer thicknesses of material, providing selectivity of surface contaminants from underlying material. Far less thermal plasma is created, reducing the background Planckian emission that is concurrent with species-specific spectral line emission. The unusual phenomena of self-channeling that transforms the diverging (or focused) laser beam into a ~100 μm diameter self-sustaining waveguide can project breakdown energy densities to distances of a kilometer or more.

In still another embodiment, the illumination system further includes a broad band light source 105 and a beam steering mirror 107. The broad band light source illuminates the sample in the target area with broadband light producing photons reflected from different locations on or within the unknown sample. The stirring mirror 107 functions to change the type of illumination source, from the laser light source 106 to the broad band light source 105. The laser light source 106 and broadband light source 105 are responsive to first control signals generated by processor 160, that control selection and operation of the laser light source 106 and the broadband light source 105.

Referring to FIG. 1, the first optical system is optically coupled to the laser light source 106 and the broad band light source 105. The first optical system includes beam steering mirrors 112 and 116, and telescope 114. The components of the first optical system are matched to the f-number of the secondary mirror of the telescope, and expanding the laser beam to fill the secondary mirror. The laser excitation pulse propagates along the telescope's optical axis and presents a laser spot that fills the telescope's field of view at the chosen focal point. This allows for a 180° backscattering collection geometry and enables repositioning and refocusing of the telescope 114 and laser spot simultaneously.

With reference to FIG. 1, system 100 includes a video capture device 124 that outputs a dynamic image of the target 150 in real time. The video capture device 124 provides first order targeting of explosive residues. Video is highly sensitive but has a low specificity, in that it provides a low level means of classifying objects based on morphological factors such as size, shape and color. Such first-order discrimination provides good guidance for subsequent higher order classification and detection such as LIBS spectroscopy and Raman spectroscopy/imaging. In one embodiment, the video capture device 124 uses a target scope 118 to provide the user a large field of view and zoom control for the video capture device 124.

The video capture device 124 includes a color video CCD used as a detector. This sensor provides a high fidelity digital image, typically 480 pixel×640 pixel format, and a rapid frame rate, 30 Hz. The video capture device 124 may use ambient light or light from laser light source 106 to illuminate the target area. The video capture device 124 may also collect a series of small images, that are recombined into a larger, macro-image for analysis. The video capture device 124 operates in the first order targeting mode to rapidly screen objects based on the intrinsic size, shape and color properties of the particles. Regions of interest suspected to possess explosive residues are located and identified, honing in on the target area at which to conduct further analysis using LIBS/Raman imaging spectroscopy that provide greater specificity.

In another embodiment, the video capture device 124 includes a liquid crystal tunable filter 120 to sequentially filter the photons detected by the device. In yet another embodiment, the first order targeting system includes a near infrared capture device 122 that outputs an image of the target 150. The near infrared capture device 122 uses ambient light as its light source to illuminate the target area.

The second optical system includes telescope 114, objective 126, beam splitter 128, filter 130, laser line filter 142 and lens 144. Objective 126 collects and focuses luminescence emitted photons, reflected photons, scattered photons and plasma emitted photons and directs the collected photons to beam splitter 128. The second optical system is responsive to second control signals that enable beam splitter 128 to direct the photons to filter 130 or the fiber array spectral translator device 148. Beam splitter 128 directs the collected luminescence emitted photons and collected reflected photons to filter 130. Beam splitter 128 directs the collected scattered photons and collected plasma emitted photons to fiber array spectral translator device 148. Prior to the fiber array spectral translator device 148, the collected scattered photons and collected plasma emitted photons pass through laser line filter 142 which filters out elastic scattered illumination light laser light source 110. Filter 142 enables spectrally filtering of the photons at the illuminating wavelength. The collected scattered photons and collected plasma emitted photons pass through lens 144 which focuses the collected photons onto the entrance of the fiber array spectral translator device 148.

Filter 130 is responsive to third control signals generated by processor 160, wherein the third control signals establish predetermined wavelength bands passed by filter 130. In one embodiment, filter 130 sequentially filters collected luminescence emitted photons, in each of a plurality of predetermined wavelength bands. In another embodiment, filter 130 sequentially filters collected reflected photons, in each of a plurality of predetermined wavelength bands. In yet another embodiment, filter 130 sequentially filters collected luminescence emitted photons and collected reflected photons in each of a plurality of predetermined wavelength bands. Filter 130 includes electro-optical tunable filters, liquid crystal tunable filter ("LCTF") or acousto-optical tunable filter ("AOTF"). The plurality of predetermined wavelength bands include specific wavelengths or ranges of wavelengths. In one embodiment, the predetermined wavelength bands include wavelengths characteristic of the sample undergoing analysis. The wavelengths that can be passed through tunable filter 130 may range from 200 nm (ultraviolet) to 2000 nm (i.e., the far infrared). The choice of tunable filter depends on the desired optical region and/or the nature of the sample being analyzed. Filter 130 includes a Fabry Perot angle tuned filter, an acousto-optic tunable filter, a liquid crystal tunable filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, and a liquid crystal Fabry Perot tunable filter. The tunable filer is selected to operate in one or more of the following spectral ranges: the ultraviolet (UV), visible, near infrared, and mid-infrared.

Filter 130 passes photons to a two dimensional array of detection elements. In one embodiment, filter 130 passes luminescence emitted photons to a first two-dimensional array of detection elements 140 ("first detector"). The first detector 140 detects in a spatially accurate manner photons passed by the filter which were luminescence emitted from different locations on or within the unknown sample and generates at least one of plurality of spatially resolved fluorescence spectra and a plurality of spatially accurate wavelength resolved fluorescence images. In a second embodiment, filter 130 passes reflected photons to an infrared two-dimensional array of detection elements 132 ("infrared detector"). The infrared detector 132 detects in a spatially accurate manner photons passed by the filter which were reflected from different locations on or within the unknown sample and generates a plurality of spatially accurate wavelength resolved infrared images.

In another embodiment, filter 130 passes luminescence emitted photons and reflected photons to steering mirror 136. Fourth control signals establish which detector the steering mirror 136 directs the luminescence emitted and reflected photons. In response to the fourth control signals, steering mirror 136 directs the luminescence emitted photons to lens 134 which collects and directs the luminescence emitted photons to the first detector 132. Alternatively, steering mirror 136 directs the reflected photons to lens 138 which collects and directs the reflected photons to the infrared detector 140, in response to the fourth control signals.

The first detector 132 and infrared detector 140 may include a digital device such as an image focal plane array ("FPA") or CCD or CMOS sensor. The optical region employed to characterize the sample of interest governs the choice of two-dimensional array detector. For example, a two-dimensional array of silicon charge-coupled device ("CCD") detection elements can be employed with visible wavelength fluorescence for first detector 132. Gallium arsenide (GaAs) and gallium indium arsenide (GaInAs) FPA detectors can be employed for image analyses at near infrared wavelengths for the infrared detector 140. The choice of such devices depends on the type of sample being analyzed. The first detector 132 detects, in a spatially accurate manner, the luminescence emitted photons passed by filter 130. In one embodiment, each detection element in the first two-dimensional array of detection elements used to form the detection array 132. The infrared detector 140 detects, in a spatially accurate manner, the reflected photons passed by filter 130. In one embodiment, each detection element in the first detector 132 and the infrared detector 140 is used to form the detection array.

In another embodiment, the first detector 132 and the infrared detector 140 produce digital images of the entire view of the sample as processed by filter 160.

Figure 2B:
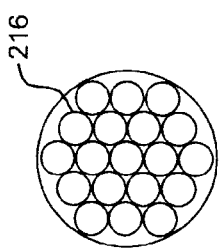
FIGS. 2A and 2B illustrate a device used in a system of the present disclosure.
Figure 2A:
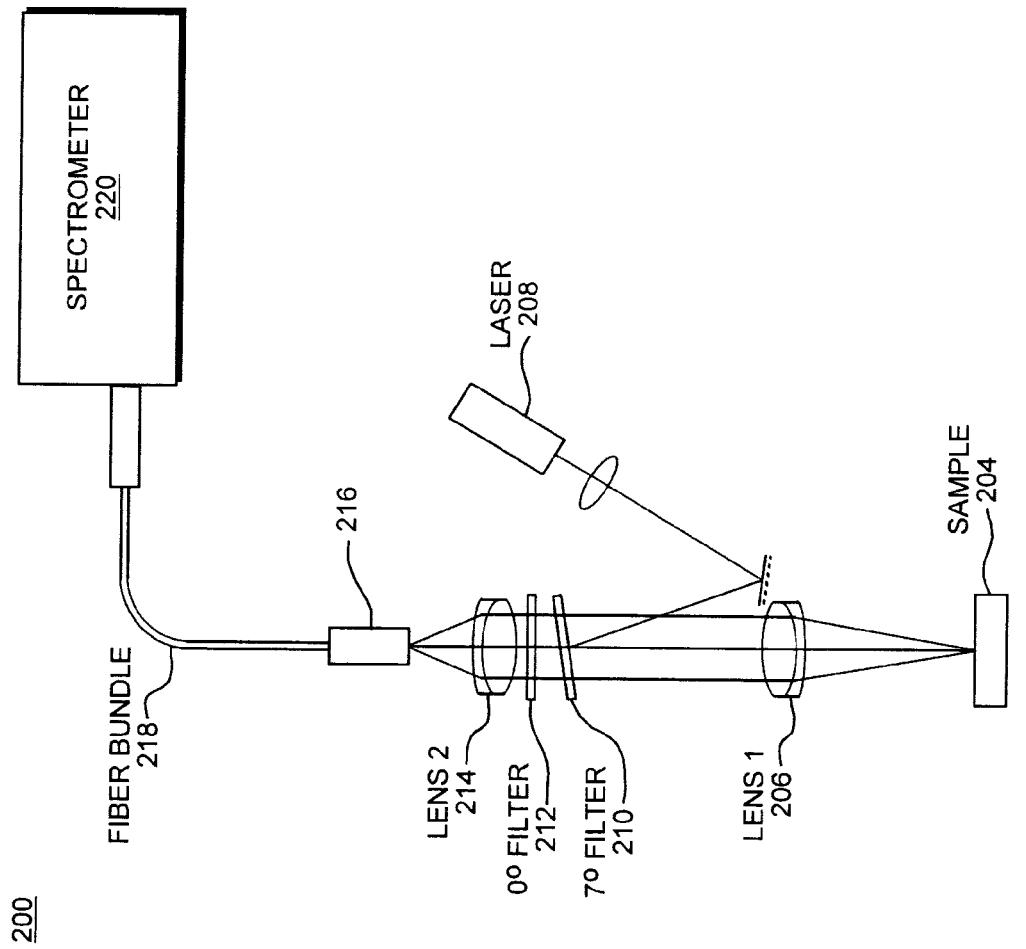

Fiber array spectral translator device 148 ("FAST") receives the collected scattered photons and collected plasma emitted photons. With reference to FIG. 2, the FAST system 148 includes a first lens 206, an illumination source 208, a first filter 210, a second filter 212 a second lens 214, a first end of a fiber bundle 216 and a second end of the fiber bundle 218 which is connected to a spectrometer 150. The first lens 206 acts as a collecting lens which focuses the illumination source onto the sample 204 and collects photons. Photons transmitted or reflected by the sample will have the same wavelength as the laser and will be blocked by filter element 212) produced by the sample 204. Lens 206 collimates the photons produced by the sample projecting the photons into infinity. The second lens 214 is used in combination with the first lens 206 to form images at the final focal plane of the second lens 214. The first end of the fiber bundle 216 is comprised of a two dimensional non-linear array of fiber bundles. The second end of the fiber bundle 218 is comprised of a curvilinear array of fiber bundles wherein curvilinear may include a straight line as well as a curved line configurations. The fiber array spectral translator device 148 may have as few as six fibers providing rough spatial resolution within the sample. In another embodiment, fiber array spectral translator device 148 may have 17 collection fibers providing rough spatial resolution within the sample. Alternatively, high spatial resolution could be achieved using as many as 30,000 individual fibers.

Referring to FIG. 1, spectrograph 150 is coupled to the fiber array spectral translator device 148. The entrance slit of the spectrograph 150 is optically coupled to the device 148 to disperse the scattered and plasma emitted photons. For the scattered photons, spectrograph 150 disperses the photons to generate a plurality of spatially resolved Raman spectra. For the plasma emitted photons, spectrograph 150 disperses the photons to generate a plurality of spatially resolved atomic spectra.

A second two-dimensional array of detection elements 152 ("second detector") is optically coupled to the spectrograph 150 to detect the plurality of spatially resolved Raman spectra and the plurality of spatially resolved atomic spectra produced by spectrograph 150. In one embodiment, the second two-dimensional array of detection elements 152 comprises a TE-cooled ICCD. Cooling the ICCD reduces the thermal electronic noise associated with the detector to enable the detection of the relatively weak Raman light emitted from the sample Photodiode 165 is optically coupled to the first optical system and generates a gating signal to synchronize the acquisition time of the second two dimensional array of detection elements with a pulse width of the laser light emanating from the laser light source 110. The photodiode 205 is positioned at the exit of the telescope 114 and triggers a delay and gate generator. This removes timing errors, which can be caused by laser Q-switch jitter, different cable lengths and/or induced noise. The acquisition time, gate width, is then set to match the laser pulse width. Raman scattered photons are only generated while the laser pulse interacts with the sample surface, as Raman scattering has no measurable "lifetime." The delay time is then set to match the range at which data is collected, twice the distance from the sample divided by the speed of light.

Still referring to FIG. 1, system 100 also includes at least one processor that generates a plurality of control signals. Processor 160 is coupled to and is used to control the optical devices of the system illustrated in FIG. 1. Processor 160 generates first control signals 162a to control the laser light source 106, the broad band light source 105. Second control signals 162b control operation of the second optical system such that the second optical system directs the collected luminescence emitted photons to a filter and directs the collected scattered photons and the plasma emitted photons to the fiber array spectral translator device processor 150, control beam splitter 128. Processor 160 is also coupled to filter 130 which is responsive to third control signals 162c generated by processor 160, wherein the third control signals establish predetermined wavelength bands passed by filter 130 to first detector 132 or the infrared detector 140 from different spatial locations on or within sample 100. The fourth control signals 162d control operation of steering mirror 136 such that it directs the luminescence emitted photons to the first detector 132, and directs the reflected photons to the infrared detector 140.

In one embodiment, system 100 operates in a luminescence emitted mode, a Raman spectroscopy mode and a laser induced break down spectroscopy mode. In another embodiment, system 100 operates in a near infrared mode, a Raman spectroscopy mode and a laser induced break down spectroscopy mode. In yet another embodiment, system 100 operates in a luminescence emitted mode, a near infrared mode, a Raman spectroscopy mode and a laser induced break down spectroscopy mode.

In the luminescence emitted mode, the first control signals control operation of the laser light source in order to produce luminescence emitted photons from different locations on or within the unknown sample. The second control signals control the operation of the second optical system such that the second optical system directs the collected luminescence emitted photons to the filter. The third control signals control operation of the filter such that the filter sequentially filters collected luminescence emitted photons, in each of a plurality of predetermined wavelength bands. The fourth control signals such that a steering mirror directs the luminescence emitted photons to the first two dimensional array of detection elements.

In the near infrared mode, the first control signals control operation of the broadband light source in order to produce photons reflected from different locations on or within the unknown sample. The second control signals control the operation of the second optical system such that the second optical system directs the collected reflected photons to the filter. The third control signals control operation of the filter such that the filter sequentially filters collected reflected photons, in each of a plurality of predetermined wavelength bands. The fourth control signals such that a steering mirror directs the reflected photons to the infrared two dimensional array of detection elements.

In the luminescence mode and near infrared mode, the regions of interest are rapidly scanned for target areas, thereby greatly reducing the time to positively identify target analytes. Although explosive materials are not fluorescent, fluorescent contaminates/byproducts produce luminescence emitted photons. The presence of this fluorescent contamination may be used to rapidly pinpointing a target area for further investigation. Near infrared imaging provides a means for screening for surface/subsurface target areas and unknown materials.

Figure 3C:
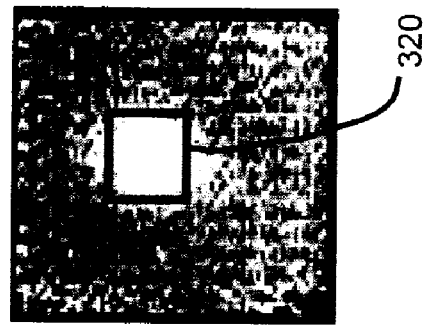
FIGS. 3A-3C illustrate a near infrared image of TNT buried in sand.
Figure 3B:
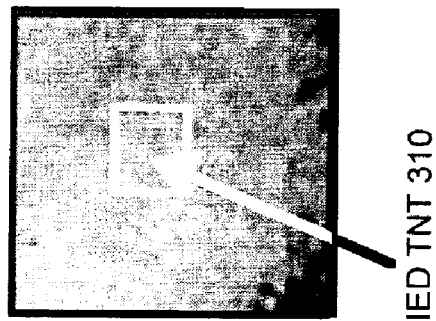
Figure 3A:
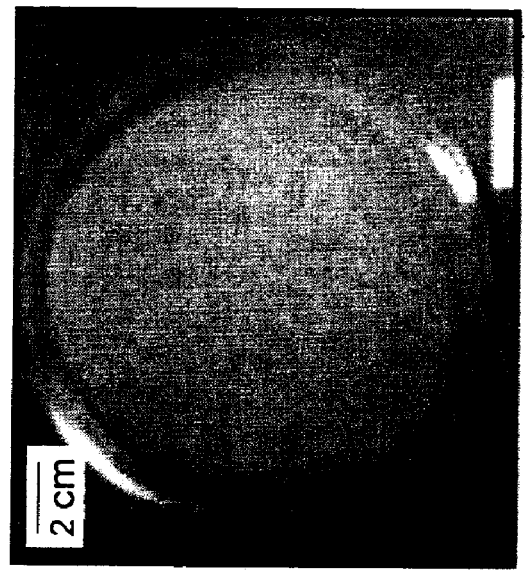

FIGS. 3A-3B illustrate the feasibility of utilizing near-infrared mode for the detection of subsurface residual explosives. TNT was placed in a Petri dish and covered with sand. The buried TNT was then placed under ChemImage's CONDOR macroscopic imaging system as illustrated in FIG. 3A. An enlarged image of the buried TNT 310 is illustrated in FIG. 3B. A near-IR chemical image was acquired of the area, in FIG. 3B, where the TNT was buried, FIG. 3C. The 1630 nm near-IR chemical image reveals the buried TNT as indicated by the boxed area 320.

To demonstrate the feasibility of utilizing a luminescence emitted mode for the detection of residual explosives, military grade C4 explosive was placed on a human hand, FIGS.

Figure 5B:
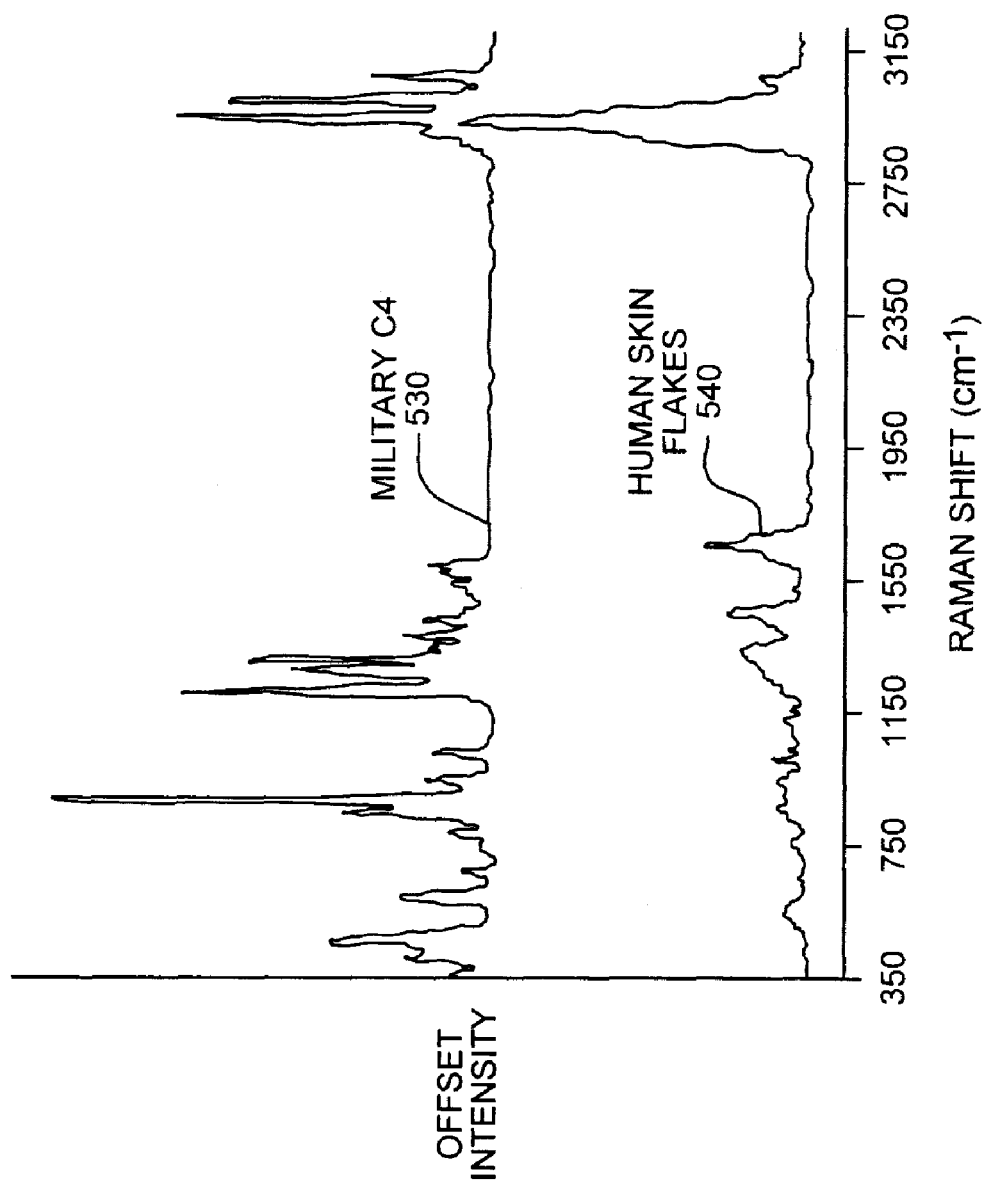

4A-4E. FIG. 4A illustrates an image of the hand obtained with ChemImage's CONDOR macroscopic imaging system. A fluorescence chemical image was acquired from an area on the skin containing two locations encircled by ink marks—one area 410 containing C4, and one area 420 without C4, FIG. 4A. Fluorescence images were collected immediately after the C4 was placed on the skin FIG. 4B, following a wipe, FIG. 4C, and after the hand was washed with soap and water, FIG. 4C. Using fluorescence imaging, even trace levels of C4 were located in area 470 compared to area 480, after the hand was washed with soap and water. These results are striking and suggest significant sensitivity to trace levels of C4, or more likely, explosives packaging materials. FIG. 5A illustrates the fluorescence spectrum of C4, 510 compared to the fluorescence spectrum of human skin 520. As illustrated in FIG. 5B, the Raman spectrum of C4, 530 is also significantly different from that of human skin 540, suggesting that Raman spectroscopy may also provide a sensitive tool for the detection of trace explosive material.

Figure 6A:
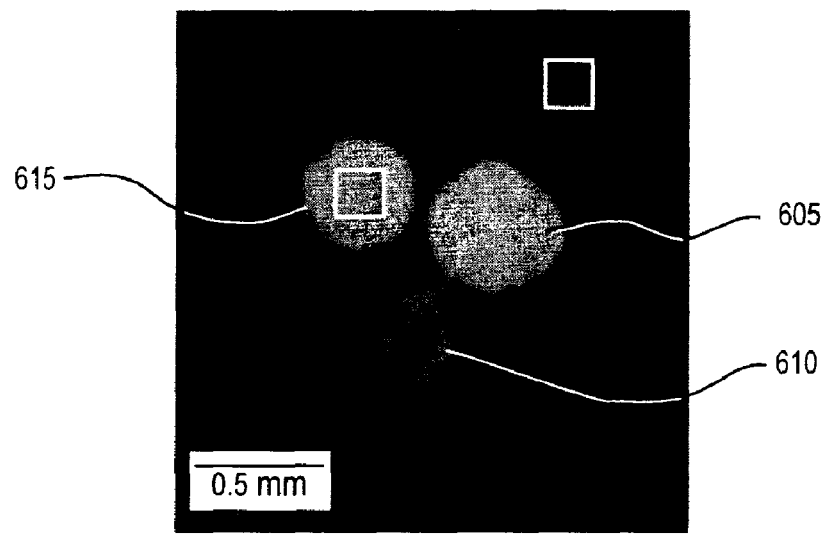
FIGS. 6A-6D illustrate fluorescence images and spectra for unfired gunpowder and fired gunpowder.
Figure 6B:
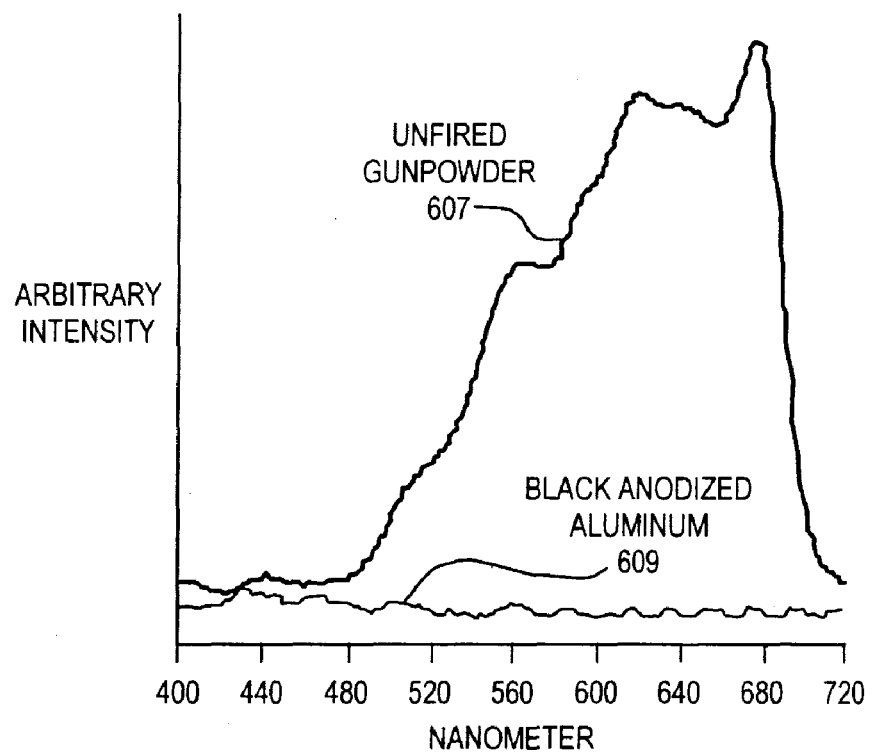
Figure 6C:
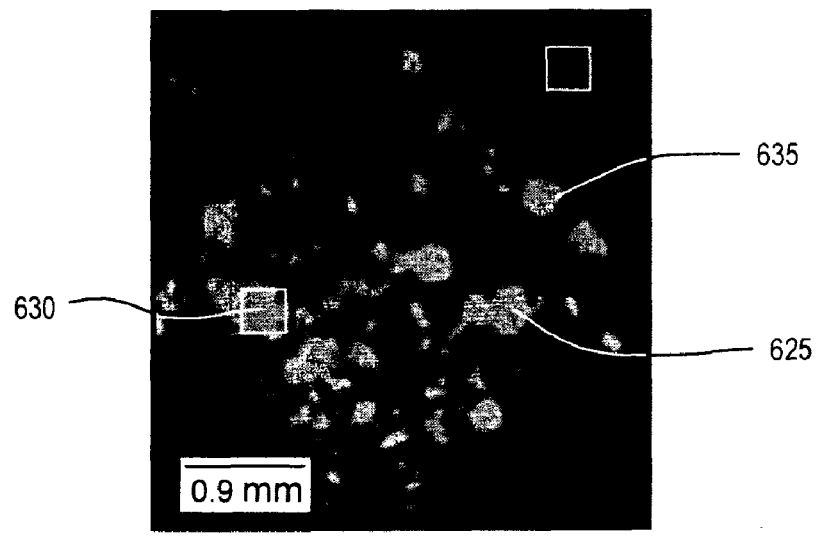
Figure 6D:
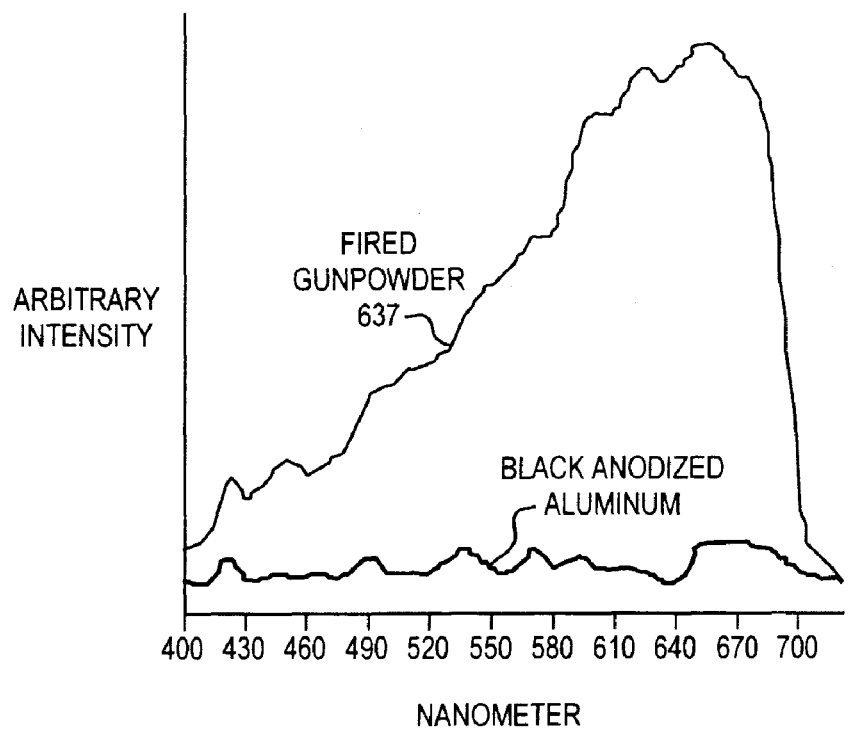

With reference to FIGS. 6A-6D, the ability of fluorescence imaging to enhance the visualization of unfired gunpowder and fired gunpowder is illustrated. FIG. 6A illustrates a fluorescence image of unfired gun powder, where the unfired gunpowder is located in areas 605, 610 and 615. The fluorescence spectrum of the unfired gunpowder 607 was obtained from area 605, and the fluorescence spectrum 609 of the anodized aluminum background was obtained from area 620, FIG. 6B. FIG. 6C illustrates a fluorescence image of fired gun powder, where the fired gunpowder is located in areas 625, 630 and 635. The fluorescence spectrum 637 of the fired gunpowder was obtained from area 630, FIG. 6D.

In the Raman mode, the first control signals control operation of the laser light source in order to produce scattered photons from different locations on or within the unknown sample. The second control signals control the operation of the second optical system such that the second optical system directs the collected scattered photons to the fiber array spectral translator device.

Figure 7:
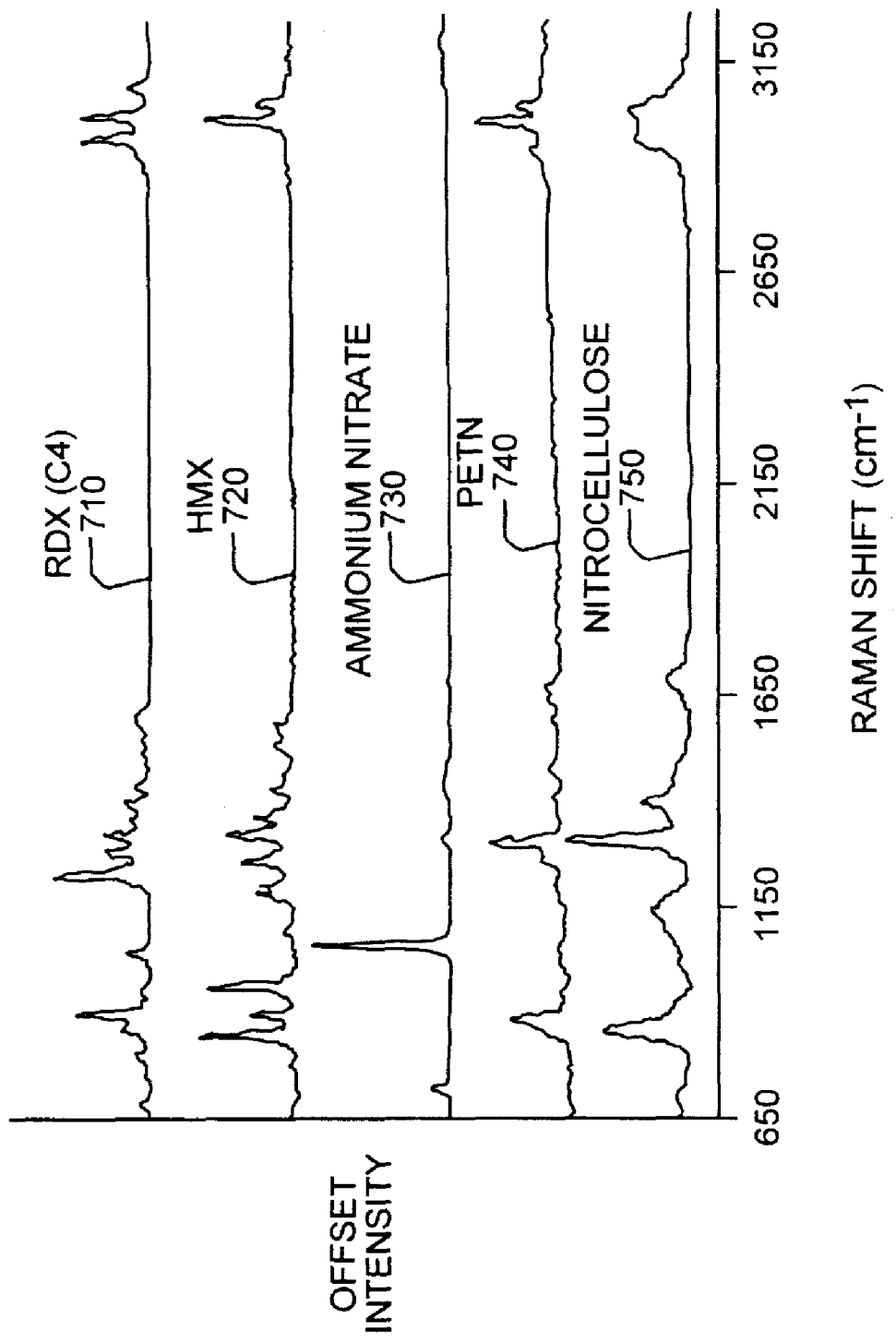
FIG. 7 illustrates Raman dispersive spectra for several explosive materials.

The capability to provide highly specific signatures from representative explosive materials in the Raman mode is illustrated in FIG. 7. The dispersive Raman spectra, include RDX (C4) 710, HMX 720, Ammonium nitrate 730, PETN 740, and nitrocellulose 750. Each material type exhibits a molecular-specific fingerprint signature. The Raman spectra are inherently richer in information In the Raman mode, Raman imaging spectroscopy is used as a tool for molecular identification. Explosive materials have strong, unique Raman spectra that are "fingerprints" of the vibrational spectrum of the molecule. This mode differentiates between two very similar molecules, and to differentiate between a target analyte and it's matrix. Using the fiber array translator device provides low pixel fidelity spatially resolved Raman dispersive spectral images and improved reliability of detecting target analytes from a deposited mixture of particles.

In the LIBS mode, the first control signals control operation of the laser light source in order to produce plasma emitted photons from different locations on or within the unknown sample. The second control signals control the operation of the second optical system such that the second optical system directs the collected plasma emitted photons to the fiber array spectral translator device.

Figure 8:
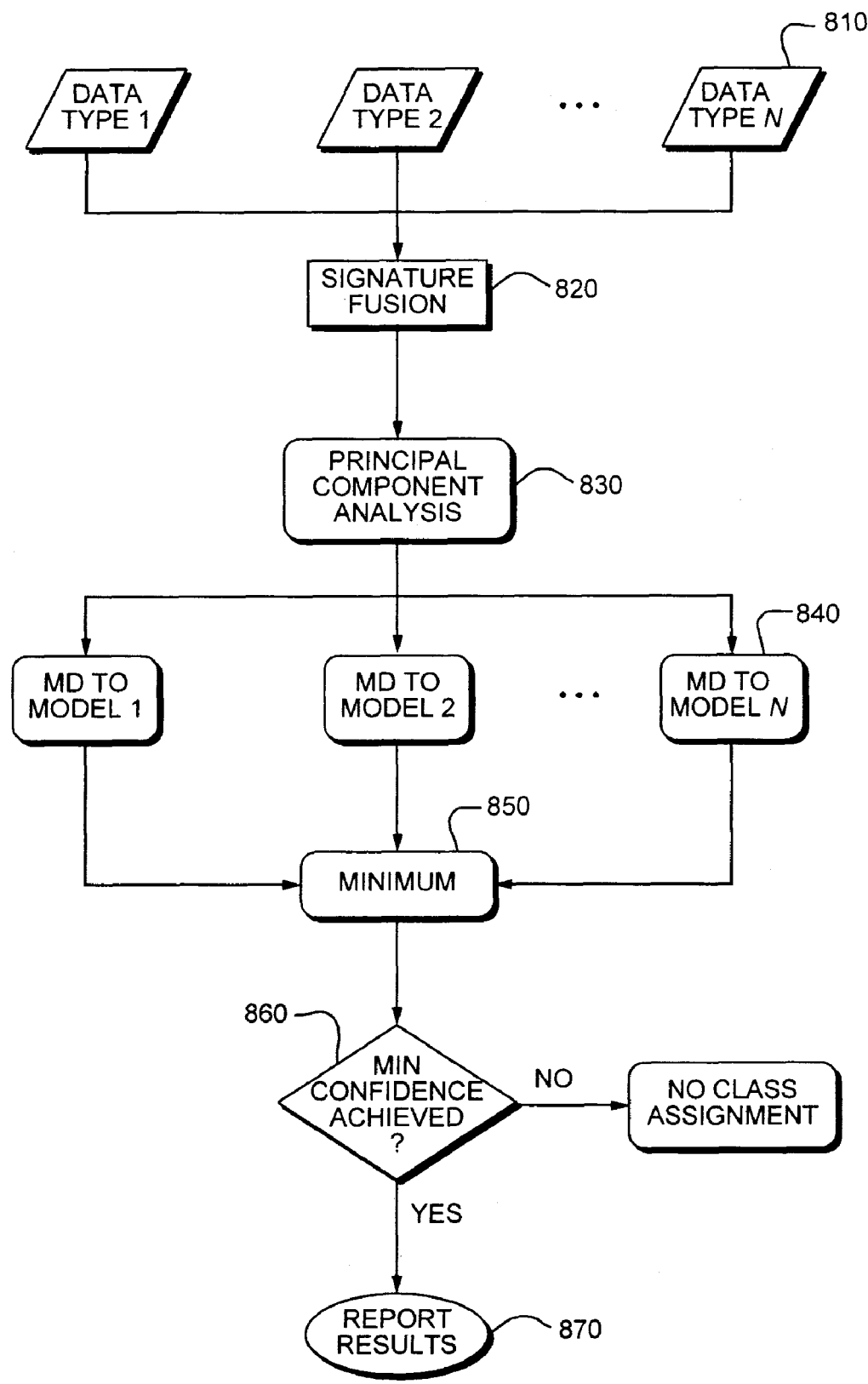
FIG. 8 illustrates an exemplary data analysis scheme used in a method of the present disclosure.

System 100 further includes instructions executable by at least one processor that applies a fusion algorithm to two or more data types including spatially resolved fluorescence spectra, the plurality of spatially resolved Raman spectra and the plurality of spatially resolved atomic spectra, in order to identify the unknown sample. In one embodiment, the multiple data types are fused and then searched relative to a signature library or Data Fusion Then Search. As illustrated in FIG. 8, the multiple data types are fused by concatenating the corresponding multiple spectra into combined data, 820. Principal Component Analysis was then performed on the combined data to identify the important features, 830. Models of the class data were then created, using a similarity metric, 840. The model data are examined to determine if a minimum confidence is achieved, 860. If a minimum confidence is achieved, the results are reported, 870. If a minimum confidence is not achieved, no class assignment is made. In one embodiment, the minimum confidence value may range from 0.70 to 0.95. In another embodiment, the minimum confidence value ranges from 0.8 to 0.95. In yet another embodiment, the minimum confidence value ranges from 0.90 to 0.95.

Figure 9:
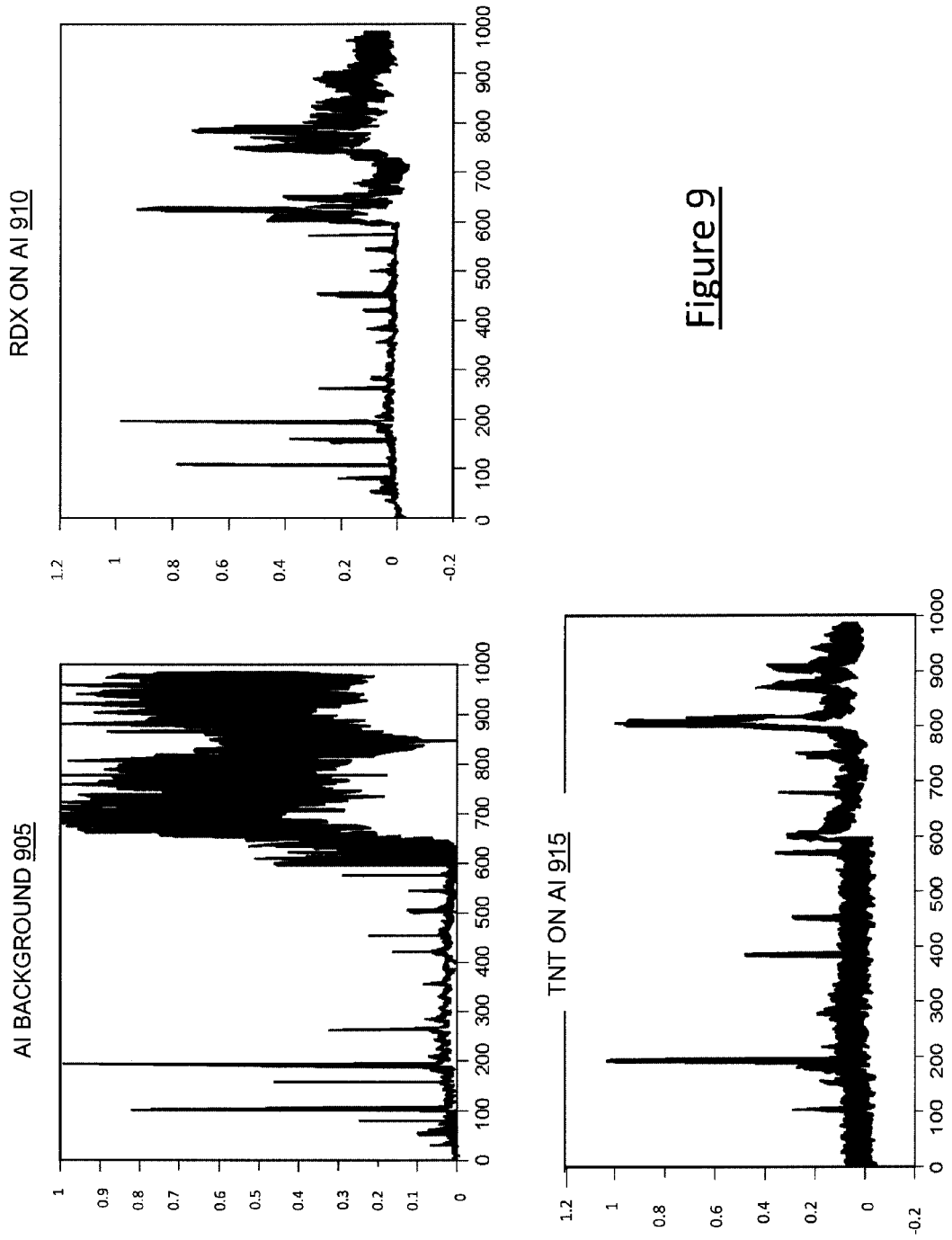
FIG. 9 illustrates Raman and LIBS spectra for RDX and TNT on an aluminum substrate.

Results from the Data Fusion Then Search (DFTS) approach are shown in FIG. 9. Raman and LIBS spectra were obtained for aluminum substrate, RDX on the aluminum substrate and TNT on the substrate. At least ten (10) Raman and LIBS spectra were obtained for material. The spectra were fused and evaluated using confusion matrices. The fusion was performed by concatenating the corresponding LIBS and Raman spectra into combined data. Principal Component Analysis was then performed on the combined data to identify the important features. Models of the class data were then created, using Mahalanobis distance as the metric. The training data were sent back through these models resulting in confusion matrices that quantify the power of the classifier. A perfect classifier results in 1's along the diagonal and 0's in the off-diagonal terms.

Figure 10A:
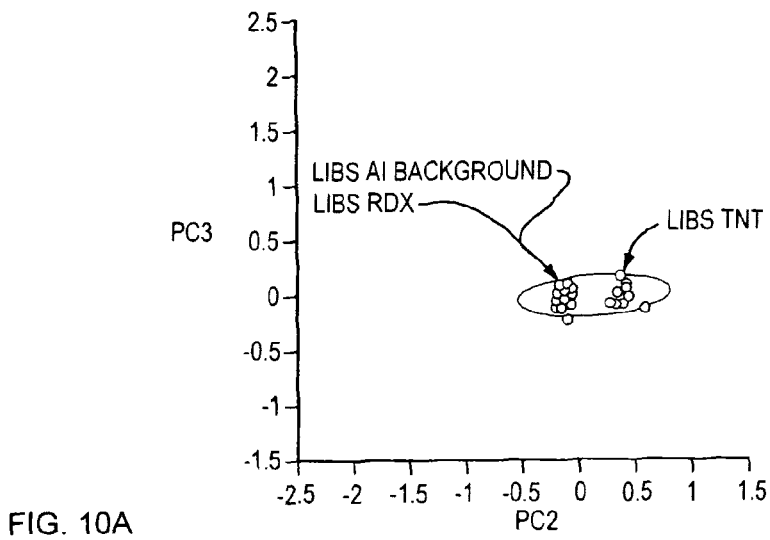
FIGS. 10A-10C illustrate the principal component scatter plots for LIBS alone, Raman alone and the fused techniques.
Figure 10B:
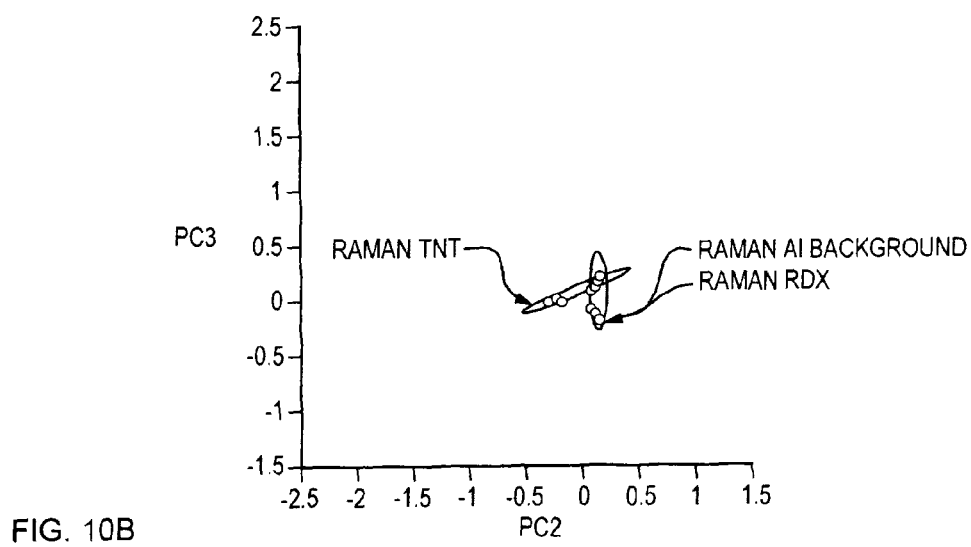
Figure 10C:
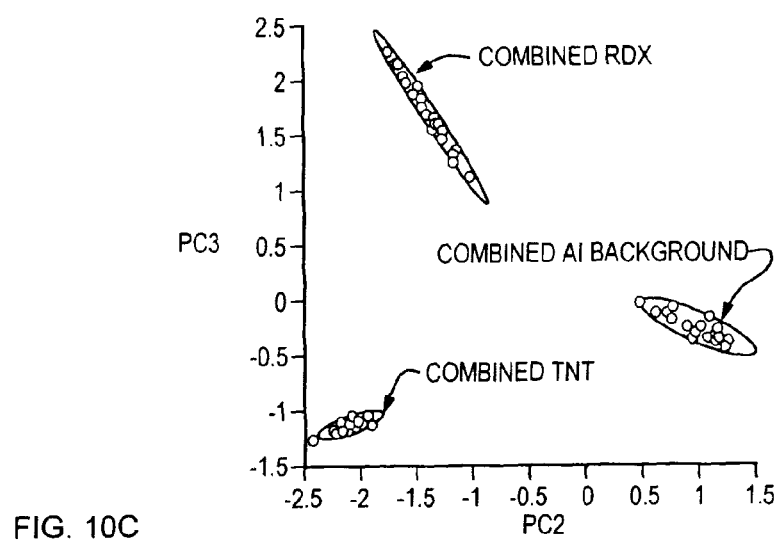
Figure 11:
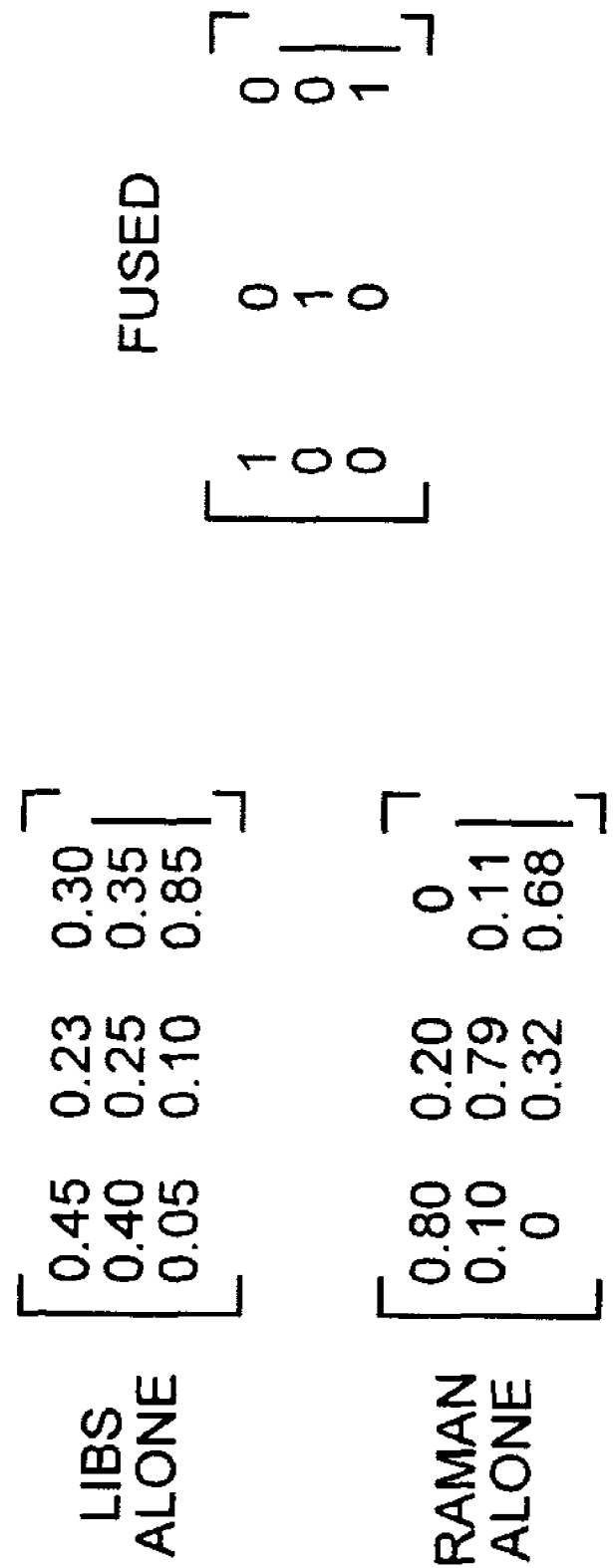
FIG. 11 illustrates the confusion matrices for LIBS alone, Raman alone and the fused techniques.

FIG. 10 illustrates the principal component scatter plots demonstrating that the DFTS sensor data fusion results exhibit improved performance relative to LIBS operating alone or Raman operating alone. Better performance is evident from the J3 criterion calculated for the combined (fusion) results compared to Raman and LIBS operating alone. The J3 criterion is a measure of discrimination and is a ratio of interclass to intraclass variability. A high J3 value reflects greater discrimination between materials. LIBS operating alone had a J3 value of 2.736426, FIG. 10A. Raman operating alone had a J3 value of 4.759002, FIG. 10B. The combined results, FIG. 10C, had a J3 value of 192.306435, a factor of 2× greater J3 value than each of the LIBS or Raman data alone. Another measure of improved discrimination performance is the diagonal terms from the confusion matrices, FIG. 11. Test data indicated that the fused LIBS and Raman data produced superior confusion matrices relative to the LIBS or Raman data taken individually through the same process.

In the case of mixture unknown, the search is performed using a spectral unmixing metric that compares a plurality of spectra for the unknown to library spectra. A spectral unmixing metric is disclosed in U.S. patent application Ser. No. 10/812,233 entitled "Method for Identifying Components of a Mixture via Spectral Analysis," filed Mar. 29, 2004 which is incorporated herein by reference in its entirety.

The system of the present disclosure may be used to identify unknown materials located above the ground. An above ground area is surveyed to identify a region of interest based on at least one of size, shape and color of the region of interest. The region of interest is illuminated with a plurality of photons producing emitted photons from the region of interest. The emitted photons, produced by the region of interest, are analyzed using fluorescence spectroscopy to produce at least one of the following: a plurality of spatially resolved fluorescence spectra and a plurality wavelength resolved fluorescence images. To identify a target area, one or both of the plurality of spatially resolved fluorescence spectra and the plurality wavelength resolved fluorescence images are used. The target area is then illuminated with a plurality of photons producing Raman scattered photons and plasma emitted photons from the target area. Using a fiber array spectral translator device, Raman scattered photons and plasma emitted photons produced by the target area are collected. The fiber array spectral translator device comprises a two dimensional non-linear array of optical fibers drawn into a one dimensional fiber stack that converts a two-dimensional field of view into a curvilinear field of view, wherein the one dimensional fiber stack is coupled to an entrance slit of an imaging spectrometer. The Raman scattered photons, produced by the target area, are analyzed using Raman spectroscopy to produce a plurality of spatially resolved Raman spectra. The plasma emitted photons, produced by the target area, are analyzed using laser induced breakdown spectroscopy to produce a plurality of spatially resolved atomic spectra. To identify one or more chemical compounds in the target area, a fusion algorithm is applied to at least two of the following: the plurality of spatially resolved fluorescence spectra, the plurality of spatially resolved Raman spectra and the plurality of spatially resolved atomic spectra.

The system of the present disclosure may be used to identify unknown materials located under the ground. A below ground area is surveyed to identify a region of interest based on at least one of size, shape and color of the region of interest. The region of interest is illuminated with a plurality of photons producing reflected photons from the region of interest. The reflected photons, produced by the region of interest, are analyzed using near infrared spectroscopy to produce a plurality wavelength resolved near infrared images. To identify a target area, one or both of the plurality of spatially resolved near infrared spectra and the plurality wavelength resolved near infrared images are used. The target area is then illuminated with a plurality of photons producing Raman scattered photons and plasma emitted photons from the target area. Using a fiber array spectral translator device, Raman scattered photons and plasma emitted photons produced by the target area are collected. The fiber array spectral translator device comprises a two dimensional non-linear array of optical fibers drawn into a one dimensional fiber stack that converts a two-dimensional field of view into a curvilinear field of view, wherein the one dimensional fiber stack is coupled to an entrance slit of an imaging spectrometer. The Raman scattered photons, produced by the target area, are analyzed using Raman spectroscopy to produce a plurality of spatially resolved Raman spectra. The plasma emitted photons, produced by the target area, are analyzed using laser induced breakdown spectroscopy to produce a plurality of spatially resolved atomic spectra. To identify one or more chemical compounds in the target area, a fusion algorithm is applied to at least two of the following: the plurality of spatially resolved fluorescence spectra, the plurality of spatially resolved Raman spectra and the plurality of spatially resolved atomic spectra.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method comprising:
(a) surveying an area to identify a region of interest comprising an unknown material wherein said identification of said region of interest is based on at least one of size, shape and color of said region of interest;
(b) illuminating the region of interest with a plurality of photons to thereby produce photons reflected from different locations on or within the unknown sample in said region of interest;
(c) collecting said reflected photons using short wave infrared spectroscopy to produce at least one of the following: a plurality of spatially resolved short wave infrared spectra and a plurality of wavelength resolved short wave infrared images;
(d) analyzing at least one of said a plurality of spatially resolved short wave infrared spectra and a plurality wavelength resolved short wave infrared images to thereby determine a target area:
(e) illuminating said target area with a plurality of photons to thereby produce Raman scattered photons and plasma emitted photons from the target area;
(f) collecting, via a fiber array spectral translator device, Raman scattered photons and plasma emitted photons produced by the target area, wherein said device comprises a two dimensional array of optical fibers drawn into a one dimensional fiber stack so as to effectively convert a two-dimensional field of view into a curvilinear field of view;
(g) analyzing the Raman scattered photons, produced by the target area, using Raman spectroscopy to produce a plurality of spatially resolved Raman spectra;
(h) analyzing the plasma emitted photons, produced by the target area, using laser induced breakdown spectroscopy to produce a plurality of spatially resolved atomic spectra; and
(i) applying a fusion algorithm to at least two of the following to identify one or more chemical compounds in the target area: the plurality of spatially resolved infrared spectra, the plurality of spatially resolved Raman spectra and the plurality of spatially resolved atomic spectra, wherein steps (a)-(i) are performed at a standoff distance from said unknown material.

2. A method comprising:
(a) surveying an area to identify a region of interest comprising an unknown material wherein said identification of said region of interest is based, on at least one of size, shape and color of said region of interest;
(b) illuminating the region of interest with a plurality of photons to thereby produce photons reflected from different locations on or within the unknown sample in said region of interest;
(c) collecting said reflected photons using infrared spectroscopy to produce at least one of the following: a plurality of spatially resolved infrared spectra and a plurality wavelength resolved infrared images;
(d) analyzing at least one of said a plurality of spatially resolved infrared spectra and a plurality wavelength resolved infrared images to thereby determine a target area;
(e) illuminating said target area with a plurality of photons to thereby produce Raman scattered photons and plasma emitted photons from the target area;
(f) collecting, via a fiber array spectral translator device, Raman scattered photons and plasma emitted photons produced by the target area, wherein said device comprises a two dimensional array of optical fibers drawn into a one dimensional fiber stack so as to effectively convert a two-dimensional field of view into a curvilinear field of view;
(g) analyzing the Raman scattered photons, produced by the target area, using Raman spectroscopy to produce a plurality of spatially resolved Raman spectra;
(h) analyzing the plasma emitted photons, produced by the target area, using laser induced breakdown spectroscopy to produce a plurality of spatially resolved atomic spectra; and
(i) applying a fusion algorithm to at least two of the following to identify one or more chemical compounds in the target area: the plurality of spatially resolved infrared spectra, the plurality of spatially resolved Raman spectra and the plurality of spatially resolved atomic spectra, wherein steps (a)-(i) are performed at a standoff distance from said unknown material.

3. The method of claim 2 wherein said area comprises at least one of: an above ground area and a below ground area.

4. The method of claim 2 wherein said unknown material comprises at least one of an explosive material, an explosive residue, and a chemical compound.

5. The method of claim 2 wherein said surveying comprises using a video capture device.

6. The method of claim 5 wherein said video capture device outputs a dynamic image of said area.

7. A method comprising:
(a) surveying an area to identify a region of interest comprising an unknown material wherein said identification of said region of interest is based on at least one of size, shape and color of said region of interest;
(b) illuminating the region of interest with a plurality of photons to thereby produce photons reflected from different locations on or within the unknown sample in said region of interest;
(c) collecting said reflected photons using short wave infrared spectroscopy to produce at least one of the following: a plurality of spatially resolved short wave infrared spectra and a plurality of wavelength resolved short wave infrared images;
(d) analyzing at least one of said a plurality of spatially resolved short wave infrared spectra and a plurality wavelength resolved short wave infrared images to thereby determine a target area;
(e) illuminating said target area with a plurality of photons to thereby produce Raman scattered photons from the target area; and
(f) collecting said Raman scattered photons using Raman spectroscopy to produce at least one of the following: a plurality of spatially resolved Raman spectra, a plurality of wavelength resolved Raman images, and combinations thereof, wherein steps (a)-(f) are performed at a standoff distance from said unknown material.

8. The method of claim 7 further comprising analyzing at least one of said plurality of spatially resolved Raman spectra and said plurality of wavelength resolved Raman images to thereby identify said unknown materials.

9. The method of claim 7 further comprising collecting said Raman scattered photons via a fiber array spectral translator device, wherein said device comprises a two dimensional array of optical fibers drawn into a one dimensional fiber stack so as to effectively convert a two dimensional field of view into a curvilinear field of view.

10. The method of claim 2 wherein said a plurality of spatially resolved infrared spectra comprise short wave infrared spectra and said plurality wavelength resolved infrared images comprise short wave infrared images.

* * * * *